(12) United States Patent
Byrnes et al.

(10) Patent No.: US 6,405,414 B1
(45) Date of Patent: *Jun. 18, 2002

(54) COILING CLIP AND IMPROVED SPIRAL WOUND DISPENSER

(75) Inventors: Raymond A. Byrnes, Providence; Robert A. DiPetrillo, Narragansett, both of RI (US)

(73) Assignee: Contech Packaging, Inc., Providence, RI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/314,706

(22) Filed: May 19, 1999

(51) Int. Cl.[7] ............................................. B65D 83/02
(52) U.S. Cl. ........................................ 24/339; 24/562
(58) Field of Search .................. 206/364; 128/DIG. 26; 24/339, 556, 561, 562, 16 R, 531; 242/129; 439/501; 600/585; 604/528; 248/74.2, 68.1

(56) References Cited

U.S. PATENT DOCUMENTS

| | | | | |
|---|---|---|---|---|
| 268,407 A | * | 12/1882 | Hughes | |
| 3,113,363 A | * | 12/1963 | Fyvie | |
| 3,126,184 A | * | 3/1964 | Kropp | |
| 3,382,545 A | * | 5/1968 | Spenner | |
| 3,636,595 A | * | 1/1972 | Wines | |
| 3,696,920 A | * | 10/1972 | Lahay | |
| 3,954,238 A | * | 5/1976 | Nivet | |
| 3,983,602 A | * | 10/1976 | Barry | |
| 4,380,103 A | * | 4/1983 | McGrath | |
| 4,407,472 A | * | 10/1983 | Beck | |
| 5,014,939 A | * | 5/1991 | Kraus et al. | |
| 5,027,478 A | * | 7/1991 | Suhr | |
| 5,263,945 A | | 11/1993 | Byrnes | |
| 5,309,604 A | * | 5/1994 | Poulsen | |
| 5,366,444 A | * | 11/1994 | Martin | |
| 5,735,821 A | * | 4/1998 | Dobkin | |
| 5,746,202 A | * | 5/1998 | Pagan | |
| 5,755,225 A | * | 5/1998 | Hutson | |
| 6,047,825 A | * | 4/2000 | Samuels | |

FOREIGN PATENT DOCUMENTS

| | | | |
|---|---|---|---|
| GB | 1376738 | * | 12/1974 |
| JP | 7-310865 | * | 11/1995 |

OTHER PUBLICATIONS

Contech Medical International, LTD., catalog, undated.

* cited by examiner

Primary Examiner—James R. Brittain
(74) Attorney, Agent, or Firm—Nixon Peabody LLP

(57) ABSTRACT

The clip of the present invention is a one-piece plastic clip having a plurality of substantially "C" shaped socket members, for example two, wherein the interior surface is not smooth. Rather, the interior is designed to enhance the grip on the protective tube. In one preferred embodiment, the interior surface has a plurality of spaced projections extending therefrom. Other textured surfaces can be used.

6 Claims, 2 Drawing Sheets

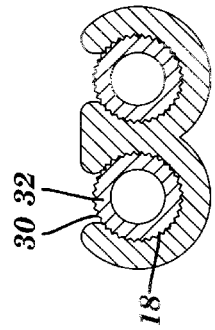
FIG. 8
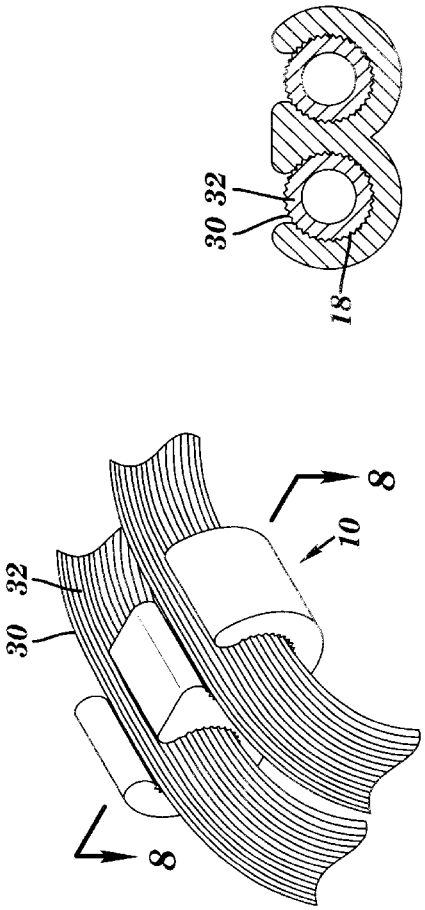
FIG. 5
FIG. 7
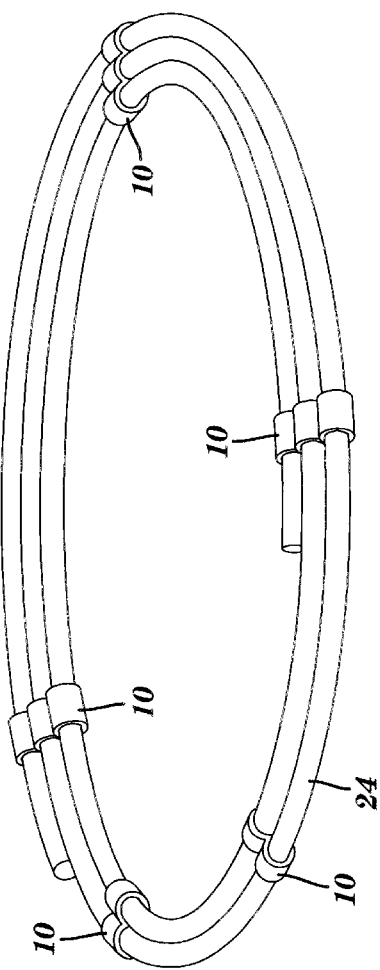
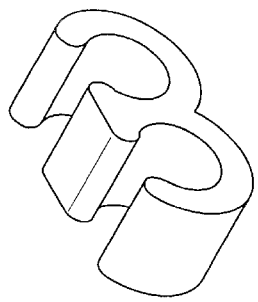
FIG. 1
PRIOR ART
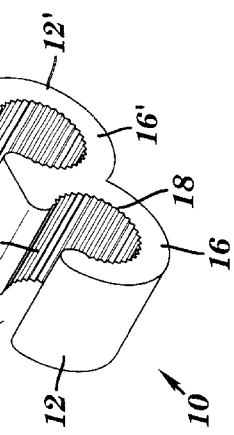
FIG. 2

COILING CLIP AND IMPROVED SPIRAL WOUND DISPENSER

FIELD OF THE INVENTION

The present invention is directed to a coiling clip that grips a plastic tube and use of that clip in a catheter dispenser.

BACKGROUND OF THE INVENTION

There are many medical procedures where catheters are used. Frequently, other apparatus is used with the catheter. For example, when a catheter is introduced into a patient's blood vessel such as an artery or vein, guidewires are routinely used.

In a typical procedure, one uses the guidewires for the positioning of a catheter. For instance in the Seldinger technique a catheter introducer is used that has a relatively short flexible cannula that is placed within the patient's blood vessel. Actual insertion of the cannula is assisted by the use of a needle that is positioned within the cannula and is thus inserted in the blood vessel. Upon insertion, the needle is withdrawn, leaving the cannula tip within the blood vessel while the body of the catheter introducer remains external of the patient.

A guidewire is then inserted through the catheter introducer and is extended through the tip of the cannula within the patient's blood vessel until it is positioned with its tip at the desired location within the patient. Upon removal of the catheter introducer, the guidewire remains in the patient and a long catheter is easily slid over the guidewire to the desired position and the guidewire withdrawn. Thus, the catheter remains within the patient having its distal end located at the proper position within the patient's blood vessel.

These catheters can be used for a variety of medical techniques including angioplasty, gene delivery, etc. Thus, the guidewires once introduced into the body can extend to distant sites.

Anytime any object is introduced into the blood stream care must be taken to insure that sterility is maintained and that the object used does not cause infection. One method by which this goal has been met is the trend to single use devices, which are sterilized when made, then shipped and ready to use.

Such guidewires are delivered through normal shipping channels and are subject to considerable handling prior to and during shipment. The guidewire itself is packaged within a protective tube in a coiled form referred to as a "spiral wound" dispenser. A typical guidewire introducer is disclosed in U.S. Pat. No. 5,282,479.

Presently, several clips or retainers referred to as "coiling clips" are used to anchor the coiled tube. These are devices having a smooth inner surface that holds the tube by exerting pressure against the tube wall. FIG. 1 illustrates a prior art clip. However, during transport it is common for a segment of the tube to "pop out" of the clip. Thus, before using the device, the physician must waste valuable time inserting the tube back into the clip. Such additional handling can not only waste time, but may compromise the sterility. This can also cause a serious problem for the physician if when using the dispenser a portion of the tube pops out of the clip. Accordingly, there is a need in the art for a coiling clip that more securely anchors the spiral wound dispenser.

SUMMARY OF THE INVENTION

The present invention provides an improved coiling clip that overcomes the aforesaid difficulties by providing an increased grip on the protective tube. The improved clip comprises a one-piece plastic clip for coiling a continuous linear flexible material, e.g., a protecting tube, comprising:

(a) two substantially "C"-shaped socket members, said socket members having a radius portion that is effective for snugly receiving and releasably holding an elongated piece of linear flexible material which has a circular cross section, said radius portion not being smooth, more preferably being textured, most preferably having extending therefrom a plurality of spaced projections; and (b) said socket members being connected in side-by-side relationship to hold a pair of linear flexible material portions in the same plane extending through the center of the socket members and in an adjacent relationship with respect to each other. The projections engage the tubing as the tubing is pushed into the clip in order to provide an increased grip by being impressed into the material of the tubing.

In a preferred embodiment, the projections are spaced parallel ribs extending from the surface of the radius.

In one preferred embodiment the two substantially "C"-shaped members are disposed with both open ends facing in the same direction. In another embodiment the two substantially "C"-shaped members are disposed with the open end of one member facing in one direction and the open end of the other member facing in the opposite direction.

The present invention further includes a method for producing a spiral wound dispenser. The method comprises inserting a portion of a protective tube into a socket of a clip of the present invention; coiling the tube; and inserting a second portion of the tube into an adjacent socket of the clip.

BRIEF DESCRIPTION OF THE DRAWINGS

FIG. 1 is a perspective view of a coiling clip of the prior art.

FIG. 2 is a perspective view of a coiling clip of the present invention.

FIG. 5 is a perspective view of a spiral wound dispenser made using a coiling clip of the present invention.

FIG. 7 is a perspective view of a coiling clip of the present invention engaging a grooved protective tube.

FIG. 8 is a cross-sectional view taken substantially along line 8—8 in FIG. 7.

DETAILED DESCRIPTION OF THE INVENTION

The clip of the present invention is a one-piece plastic clip having a plurality of substantially "C" shaped socket members, for example two, wherein the interior surface is not smooth. Rather, the interior is designed to enhance the grip on the protective tube. In one preferred embodiment, the interior surface has a plurality of spaced projections extending therefrom. Other textured surfaces can be used.

Figure 3:
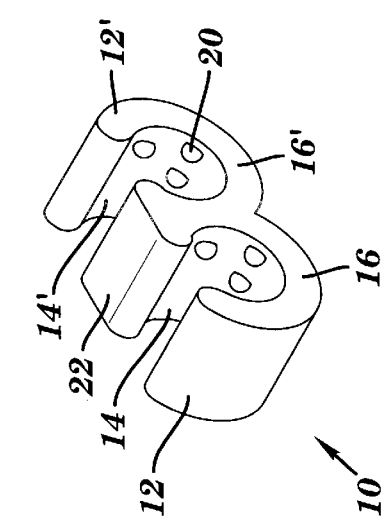
FIG. 3 is a perspective view of another embodiment of the present invention.

FIG. 2 illustrates a first embodiment of the invention in which a one piece plastic coiling clip 10 is provided with two side-by-side "C"-shaped sockets 11 and 11' which are open at one end thereof and capable of securing an initial loop of a tube which is to be coiled. In other embodiments three, four or more "C" shaped sockets can be used. The clip 10 comprises a first socket having an outer wall 12 and an inner wall 14. The bottom ends of the wall 12 and 14 are connected by an integral transverse portion 16. The walls 12 and 14 and the interconnecting transverse portion 16 provide a "C"-shaped socket which is substantially circular in cross-section, as viewed from the end of the clip and forms a radius portion along inner 14. The radius portion has extending therefrom a plurality of space projections 18. As illustrated in FIG. 2, the projections can be parallel ribs. Alternatively, as illustrated in FIG. 3, the projections can be small protuberances 20 having a generally spherical surface contour. A second adjacent "C"-shaped socket is formed by a second set of walls 12' and 14', which are joined at the bottom by a transverse portion 16' to provide an open upper end. Each of the "C"-shaped sockets is joined to one another by an intermediate section 22 that extends there between.

Figure 4:
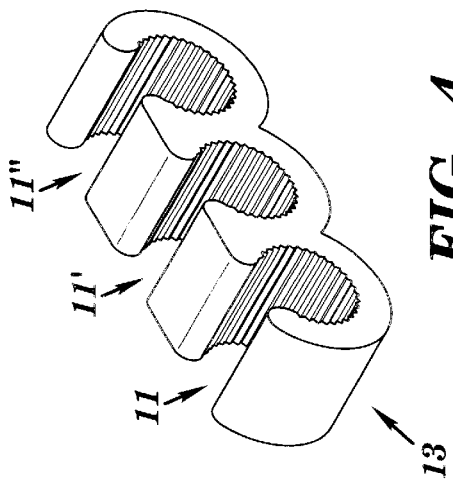
FIG. 4 is a perspective view of a further embodiment of the present invention.

Additional sockets can be integrally formed with the first two sockets. For example, as illustrated in FIG. 4, a clip 13 with three "C" shaped sockets 11, 11' and 11" can be produced.

The coiling clip may be made of any suitable material, which has a strong and flexible quality and can withstand all standard sterilization methods. Such materials include High Density Polyethylene (HDPE), Low Density Polyethylene (LDPE), Polypropylene (PP), Poly Vinyl Chloride (PVC) Polycarbonate or any other Polyolefin material used for extrusion or injection molding, including various blends. The clip can be formed using an extrusion process or can be injection molded. Extrusion is preferred.

Figure 6:
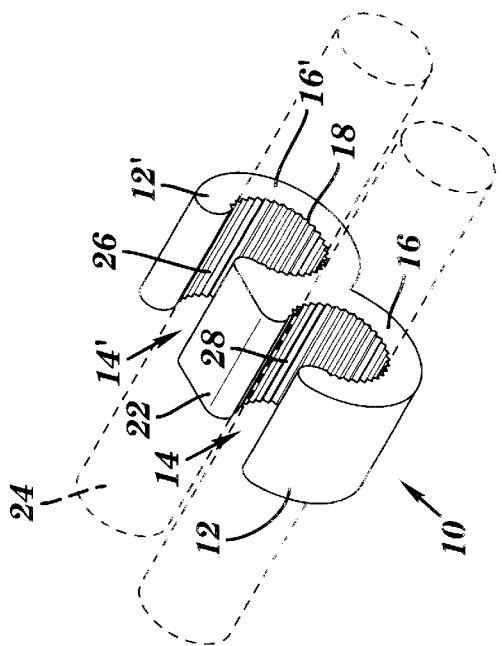
FIG. 6 is a perspective view of a coiling clip of the present invention engaging a protective tube.

FIGS. 5 and 6 illustrates the use of the clip 10 of the present invention for coiling purposes. The numeral 24 generally designates a conventional protective tube, which is to be coiled. A portion of the tube indicated by the numeral 26 is pressed downwardly into one of the sockets of the clip. The side wall (14') would spring out to receive the tube portion 26 and would then exert and inwardly directed gripping pressure on the tube portion 26. The first or initial loop is then made and the desired point in the tube length is indicated by the number 28, is pressed into an adjacent socket to form the first or initial loop. In accordance with the present invention, the projections 18 increase the grip on the tube reducing the potential for accidental tube release. The clip pressure combined with the projections impress indentations on the surface of the tube further increasing the grip of the clip on the tube.

The coiling clip of the present invention may also be made in different sizes for use with different diameter linear flexible materials.

In another embodiment the protective tube is adapted to enhance the grip of the clip. For example, as illustrated in FIGS. 7 and 8, the protective tube 30 has a plurality of minute grooves or striations 32 on the surface. The striations are preferably complementary to the parallel ribs such that the grooves 32 and the ribs 18 engage or mesh, as seen more clearly in FIG. 8, in effect "locking" the tube within the clip.

From the foregoing disclosure and detailed description of certain preferred embodiments, it will be readily apparent to those skilled in the art that various modifications, additions and other alternative embodiments are possible without departing from the true scope and spirit of the invention. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A package for protecting a catheter guidewire during shipping and handling, the package comprising:

a flexible catheter guidewire dispenser having a circular cross-section; and at least one plastic clip anchoring the dispenser in a spiral wound configuration, wherein said clip includes at least two substantially "C"-shaped socket members each disposed side-by-side with both open ends facing in the same direction, said socket members having a radius portion snugly and releasably receiving a portion of said dispenser in the same plane extending through the center of the socket members, wherein each of said radius portions including a plurality of spaced parallel ribs disposed along an entire surface thereof, said plurality of ribs being equally spaced about said radius portion and having a constant cross-section along an axial length thereof to provide an even gripping force about the entire circumference of the dispenser.

2. The package of claim 1, wherein each of the clips include a third socket member.

3. The package of claim 1, wherein the dispenser is adapted to enhance the grip of the clips.

4. The package of claim 3, wherein the dispenser comprises a plurality of grooves disposed on its surface for receiving the plurality of ribs of said at least clip.

5. A method for producing a spiral wound dispenser comprising the steps of:

providing a protective tube and at least one clip, the clip including at least two substantially "C"-shaped socket members that are disposed with both open ends facing in the same direction, said socket members having a radius portion that is effective for snugly receiving and releasably holding an elongated piece of the protective tube, said radius portion having a plurality of spaced parallel ribs disposed along an entire surface thereof, said plurality of ribs being equally spaced about said radius portion and having a constant cross-section along an axial length thereof to provide an even gripping force about the entire circumference of the protective tube, said socket members being connected in side-by-side relationship to hold a pair of protective tube portions in the same plane extending through the center of the socket members and in adjacent relationship with respect to each other;

inserting a portion of a protective tube into a socket of said clip;

coiling said tube; and inserting a second portion of said tube into an adjacent socket of said clip.

6. The method of claim 5, wherein said protective tube is adapted to enhance the grip of the clip.

* * * * *